United States Patent [19]

Kerwin

[11] Patent Number: 4,569,087
[45] Date of Patent: Feb. 11, 1986

[54] ATHLETIC GARMENTS FOR THE INSULATION OF HEAT RADIATING FROM AND APPLICATION OF A COOLING MEDIUM TO THE LIMB OF A BODY

[75] Inventor: Donald J. Kerwin, San Jose, Calif.

[73] Assignee: Joseph M. Gagliardi, San Jose, Calif.; a part interest

[21] Appl. No.: 603,774

[22] Filed: Apr. 25, 1984

[51] Int. Cl.$^4$ .................. A41B 1/12; A41D 27/12
[52] U.S. Cl. ............................................. 2/69; 2/126
[58] Field of Search ............... 2/69, 16, 108, 59, 126, 2/22

[56] References Cited

U.S. PATENT DOCUMENTS

| | | | |
|---|---|---|---|
| 2,459,992 | 1/1949 | Cimino | 2/59 |
| 3,269,036 | 8/1966 | Parker et al. | 2/22 |
| 3,329,144 | 7/1967 | Liman | 2/59 |
| 4,145,762 | 3/1979 | Wallach | 2/69 |
| 4,229,833 | 10/1980 | Cox et al. | 2/16 |

Primary Examiner—Doris L. Troutman
Attorney, Agent, or Firm—Jack M. Wiseman

[57] ABSTRACT

An athletic garment for the insulation of heat radiated from a body extremity of a user or for the application of a cooling medium to a body extremity of a user having a limb enclosing means for enclosing the body extremity and a harness for supporting the athletic garment from the body of the user. The limb enclosing means, which may be a sleeve or a legging, encloses the body extremity for insulating the heat radiated from the limb of a user. In another embodiment, an athletic garment comprises limb enclosing means to which a pocket containing a cooling medium is attached for applying a cooling medium to the extremity.

16 Claims, 5 Drawing Figures

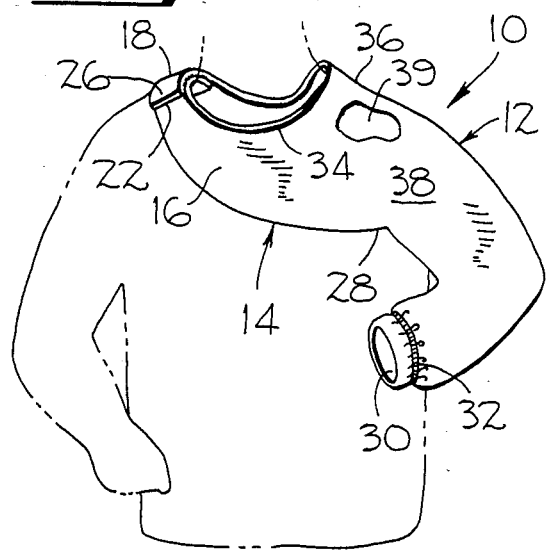
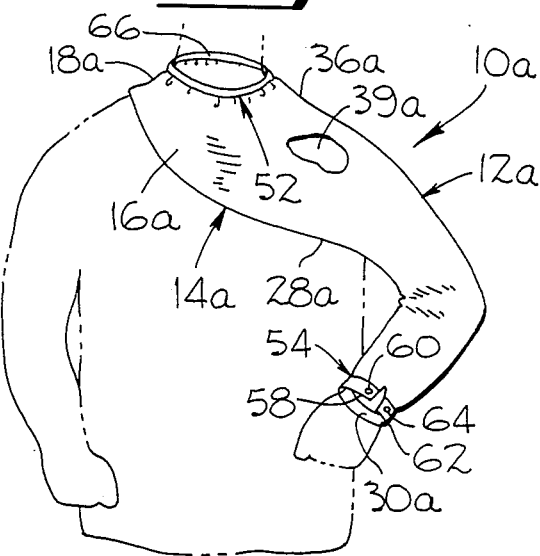
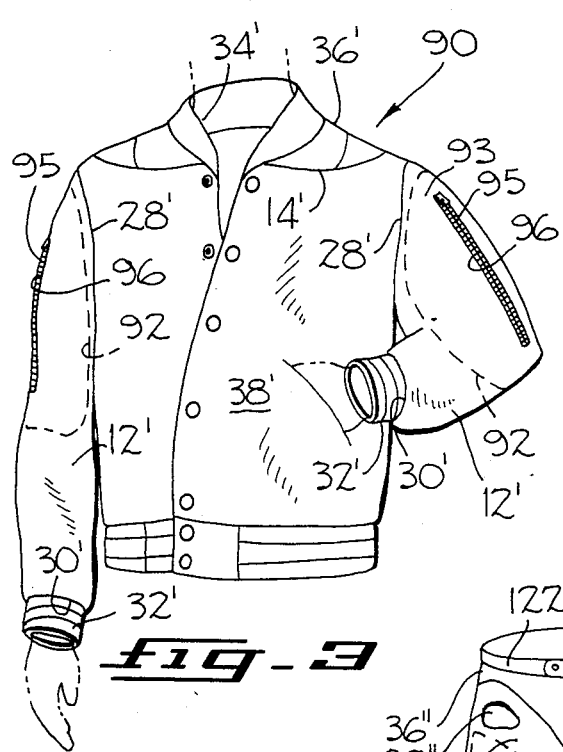
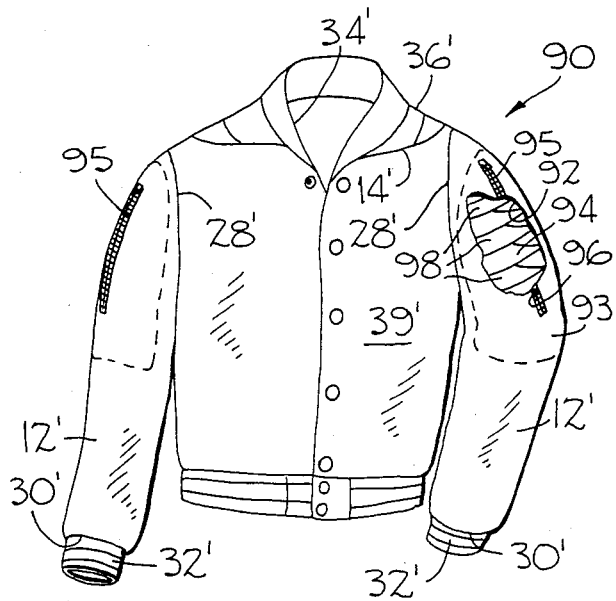
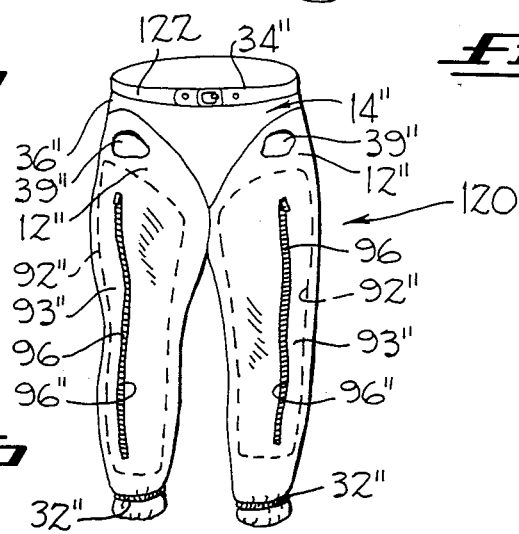

ATHLETIC GARMENTS FOR THE INSULATION OF HEAT RADIATING FROM AND APPLICATION OF A COOLING MEDIUM TO THE LIMB OF A BODY

BACKGROUND OF THE INVENTION

The present invention relates in general to athletic sports equipment, and more particularly to an article of athletic sportswear.

In the field of amateur and professional athletics, athletic competitors frequently discontinue their athletic activity for a relatively short period of time. Examples of this situation are varied and include baseball and football players, such as pitchers and quarterbacks. Other examples include those athletes who are intermittently entering and leaving a sporting event. Each of these athletes has two common problems. The first problem is retaining the warmth, flexibility and limberness in a particular muscle group and connective tissue after the muscles and tissue have been warmed-up by use. Failure to retain the warmth, flexibility and limberness in the muscles and tissue prior to returning to the competition may result in damage to the muscles and tissue. The second problem shared by these athletes is properly cooling down the muscle group and connective tissue after strenuous exertion especially when the muscles and tissue have been damaged and show signs of inflammation.

Previous solutions to the problems discussed above have been twofold. In order to retain the warmth, flexibility and limberness in the muscles and tissue, an athlete simply donned an article of clothing. Likewise, in order to properly cool down the muscles and tissue, a cooling medium of some form, such as an ice pack, was applied to the affected area.

The previous solutions to the problems described are unsatisfactory because these solutions do not provide a convenient arrangement for retaining the warmth, flexibility and limberness in or for properly cooling down the muscles and tissue. The requirement of stopping the competition to permit a player to don a jacket or sweat pants in order to retain the warmth, flexibility and limberness in the muscles and tissue was found to be inconvenient. This situation is common when the baseball pitcher becomes a baserunner. In addition to consuming time, baserunning required complete freedom of movement and thus the past solution of donning only one-half the jacket is unacceptable. The player is then required to don the entire jacket which results in discomfort in warm climates. The application of an ice pack to an injury requiring immediate cooling of the affected area to avoid excessive swelling was cumbersome.

SUMMARY OF THE INVENTION

An athletic garment for the insulation of heat radiated from a body extremity of a user or for the application of a cooling medium to a body extremity of a user having limb enclosing means for enclosing the body extremity and a harness for supporting the athletic garment from the body of the user. The limb enclosing means, which may be a sleeve or a legging, encloses the body extremity for insulating the heat radiated from the limb of a user. In another embodiment, an athletic garment comprises limb enclosing means to which a pocket containing a cooling medium is attached for applying a cooling medium to the extremity.

It is an object of the present invention to provide an improved athletic garment for the insulation of heat radiating from a limb of a body of the wearer or the application of a cooling medium to the limb of a body of the wearer.

It is a further object to provide an athletic garment which may be economically produced and which folds into a small compact unit providing convenient portability.

It is a further object to provide an athletic garment which is capable of being donned and removed rapidly.

It is a further object to provide an athletic garment containing a cooling medium for permitting immediate application to an extremity of the wearer of the garment.

It is a further object to provide an athletic garment having an asymmetrical design capable of being utilized on either side of the body.

BRIEF DESCRIPTION OF THE DRAWINGS

FIG. 1 is a front elevational view of an athletic garment embodying the present invention.

FIG. 2 is a front elevational view of a modification of the athletic garment shown in FIG. 1.

FIG. 3 is a fragmentary perspective view of another athletic garment embodying the present invention.

FIG. 4 is a fragmentary interior front elevational view of an athletic garment shown in FIG. 3.

FIG. 5 is a fragmentary front elevational view of still another athletic garment embodying the present invention.

DETAILED DESCRIPTION OF THE PREFERRED EMBODIMENTS

In FIG. 1 is illustrated a garment 10 for the insulation of heat radiating from a body extremity. The garment 10 includes a non-porous outer shell 38 and an inner insulating lining 39. The non-porous outer shell 38 inhibits the passage of air. The inner insulating lining 39 is attached to the inner wall of the shell 38 to insulate the heat radiating from the arm and shoulder of the wearer. The outer shell 38 and the lining 39 form limb enclosing means 12 and a harness 14. The harness 14 includes a harness segment 16 and a similarly configured harness segment 18. The harness segment 16 includes a detachable end having a connector 22 and the harness segment 18 includes a detachable end having a connector 26. The limb enclosing means 12 include an access opening 28, a terminal opening 30, and yieldable contraction means 32. The garment 10 further includes a band or collar 34, and a yoke 36 which are also formed by the shell 38 and the lining 39.

The limb enclosing means 12 of garment 10 are in the form of a sleeve for enclosing a body extremity, such as an arm, of the wearer. The enclosing means 12 include the access opening 28 which provides an entrance to the enclosing means 12 and the terminal opening 30 which provides an egress from the enclosing means 12. The harness 14 is connected directly to the enclosing means 12 and is used to support the garment 10 from the body of the wearer. The harness 14 is designed such that the harness segment 16 is permanently connected to the harness segment 18 at the yoke 36. The harness segment 16 is detachably connected to the harness segment 18 where the connector 22 and the connector 26 are detachably joined to permit the harness 14 to be removed from the body of the wearer and to permit the garment to be worn securely by the wearer.

The connector 22 and the connector 26 are preferably a Velcro connector and a Velcro receiver. However, a snap connector with a snap receiver or a plurality of buttons with a plurality of matching button holes or any suitable mechanical connector may be used. The collar 34 or interrupted band is disposed about the neck of the user when the detachable end of the harness segment 16 is connected to the detachable end of the harness segment 18. The yoke 36 connects the limb enclosing means 12 to the collar 34 and permits the limb enclosing means 12 to be supported about the arm and shoulder of the wearer for the insulation of heat radiating from the body of the wearer. The yieldable contraction means 32 are disposed at the terminal opening 30, which is located at the free end of the enclosing means 12. The yieldable contraction means 32 comprise an elasticized band that fits about the wrist or arm of the wearer to help retain the body heat radiating from the arm and shoulder within the enclosing means 12.

The garment 10 is a foldable compact unit and is very easily placed in a pocket of a baserunner coach, a sideline manager or carried by the athlete. The wearer simply unfolds the garment 10, exposes the access opening 28 and inserts the arm used into the limb enclosing means 12 or sleeve. Next, the yoke 36 is adjusted over the shoulder of the arm inserted into the sleeve and the collar 34 is positioned about the neck of the wearer. Then, the detachable end of the harness segment 16 is positioned over the detachable end of the harness segment 18 and the connector 22 is joined with the connector 26 to secure the harness segment 16 and the harness segment 18 in position for supporting the garment 10 from the body of the wearer. Finally, the elasticized band of the contraction means 32 is adjusted over the wrist or the arm inserted into the sleeve. The warmth, flexibility and limberness of the arm and shoulder are conveniently retained until the athlete is called upon to perform. The garment 10 may also be used initially when the athlete begins the throwing motion to accelerate the warm-up of the arm and shoulder. The limb enclosing means 12 constitute an enclosure with open ends only at the access opening 28 and the terminal opening 30.

FIG. 2 illustrates a garment 10a which is a modification of the garment 10. Parts of the garment 10 are shown with the same reference numeral but with the suffix "a". The garment 10a differs from the garment 10 in that an endless band 52 is used in lieu of the collar 34. In lieu of the yieldable contraction means 32 are an interrupted band of fabric 54, a fabric end 58 with a detachable connector 60 and a fabric end 62 with a detachable connector 64. The connectors 60 and 64 provide a detachable connection. In addition thereto, the detachable connection formed by the connectors 22 and 26 is not employed.

The interrupted band of fabric 54 is connected to the limb enclosing means 12a. The fabric end 58 and the fabric end 62 represent the free ends of the interrupted band of fabric 54. The connector 60 is connected to the fabric end 58 and the connector 64 is connected to the fabric end 62. The connector 64 joins with the connector 60 for securing the free end of limb enclosing means 12 about the wrist or arm of the wearer. The connector 60 and the connector 64 may be a snap connector with a snap receiver, a Velcro connector with a Velcro receiver, a plurality of buttons with a plurality of matching holes or any suitable mechanical device.

The endless band 52 is joined with the harness 14a and includes an elasticized piece 66 connected within the endless band 52 of the collar 34 for securing the harness 14a about the neck of the wearer. The use of the garment 10a of FIG. 2 is similar to the garment 10 of FIG. 1 except that the harness segment 16a is not detachably connected to the harness segment 18a and the yieldable contraction means 32 is replaced by the connector 60 and the connector 64. The garment 10a of FIG. 2 is slipped over the head of the wearer through the yieldable collar or endless band 52. The arm of the wearer is inserted into the access opening 28a and extends through the terminal opening 30a in a manner similar to that used with the garment 10 of FIG. 1. The garment 10 or the garment 10a may be used on either the right arm or the left arm due to the asymmetrical design and is foldable, portable and compact and may be donned and removed rapidly.

FIGS. 3 and 4 illustrate a garment 90 for the application of a cooling medium to a body extremity. Those parts included in the garment 90 which are similar in function and construction to parts included in garment 10 are identified by the same reference numeral with a prime suffix. The garment 90 comprises a liquid-proof pocket 92, a cooling medium 94, and access means 96. The pocket 92 may be formed in either or both limb enclosing means 12'.

The limb enclosing means 12' are in the form of a sleeve for accommodating an arm and include the access opening 28' which provides the entrance to the limb enclosing means 12' and the terminal opening 30' which provides the egress from the limb enclosing means 12'. The pocket 92 is attached to the inner lining 50' (FIG. 4) within the limb enclosing means 12' between the access opening 28' and the terminal opening 30'. The pocket 92 surrounds a limb, such as an arm, of the wearer. It has a generally cylindrical shape and is attached by sewing to the inside surface of the inner lining 39'.

The harness 14' is connected to the limb enclosing means 12' for supporting the garment 90 from the wearer. The collar 34' is attached to the harness 14' and provides an opening in the garment 90 for fitting around the neck of the wearer. The yoke 36' connects the limb enclosing means 12' to the collar 34'. The limb enclosing means 12' and the pocket 92 serve to cool the limb of the wearer.

The access means 96 permits external access to the pocket 92 for depositing the cooling medium 94 within and removing the cooling medium 94 from the pocket 92. A cover 93 for the pocket 92 includes the access means 96 and comprises a zipper 95 for opening and closing the cover 93. In lieu thereof, the cover 93 may include a Velcro connector or any mechanical connector suitable for containing the cooling medium 94 within the pocket 92. The yieldable contraction means 32' at the terminal opening 30' close the limb enclosing means 12' about the arm of the wearer and comprise an elasticized band. The cooling medium 94 utilized in the pocket 92 may be a reusable dry chemical packet, a reusable frozen ice packet, ice in crushed form or the like. The access means 96 has a fabric boundary area that is flush with the outer shell 38' of the limb enclosing means 12'.

The pocket 92 (FIG. 4) may be divided into a plurality of compartments 98 for holding the cooling medium 94 in selective zones or areas thereof. This feature permits the garment 90 to be used for cooling a selected region of the arm. It is apparent that the cooling medium may also be applied to a shoulder.

In lieu of yieldable contraction means a snap connector with a snap receiver, a Velcro connector with a Velcro receiver, a plurality of buttons with a plurality of matching holes or any suitable connector may be employed.

FIG. 5 illustrates a garment 120 for the application of a cooling medium to a body extremity. Those parts included in the garment 120 which are similar in function and construction to parts included in garment 10 are designated by the same reference numeral with a double prime. The garment 120 includes a belt 122. The limb enclosing means 12″ is in the form of a legging for accommodating a leg of the wearer and the harness 14″ fits about the hip or waist of the wearer. Although FIG. 5 illustrates a pair of leggings formed into pants, it is to be understood that a single legging with a single enclosing means 12″ is within the scope of the invention and would be useful to the athlete with an injured leg. A band 34″ connected to the harness 14″ fits about the waist of the wearer. The band 34″ and the belt 122 secure the garment 120 to the body of the wearer. The yoke 36″ connects the limb enclosing means 12″ to the band 34″ via the harness 14″. The yieldable contraction means 32″ are disposed at the terminal opening 30″, which provides the egress from the limb enclosing means 12″. The access opening 28″ which provides the entrance to the limb enclosing means 12″ is located adjacent to the yoke 36″. The yieldable contraction means 32″ are disposed at the free end of the enclosing means 12″ and are disposed about the leg of the wearer. Preferably, the yieldable contraction means 32″ includes an elasticized band.

Snaps, Velcro or button connectors and receivers may also be employed to receive the free end of the limb enclosing means 12″ to the leg of the wearer. The inner lining 39″ serves as an insulator for the insulation of heat radiating from the leg of the wearer. When only a single enclosing means 12″ with the inner lining 39″ and the nonporous outer shell 38″ is used, the band 34″ may form an endless belt with the elasticized band replacing the belt 122 for securing the harness 14″ to the waist of the user.

FIG. 5 also illustrates the enclosing means 12″ including the pocket 92″ connected between the inner lining 50″ and the shell 38″ at the enclosing means 12″ and, also, between the access opening 28″ and the terminal opening 30″ of the enclosing means 12″. The pocket 92″ includes the cooling medium for application to the leg. The cooling medium may be similar to the cooling medium 94. The pocket 92″ includes a cover 93″ disposed above the access means 96″. The cover 93″ has a zipper 96. In lieu of a zipper 96, a Velcro strip can be connected to the limb enclosing means 12″ for obtaining access to the pocket 92″ to hold the cooling medium 94″ in selected regions of the leg in a manner described in connection with FIGS. 3 and 4. The inner lining 39″ extending along the enclosing means 12″ including the pocket 92″ acts as an insulator of the cooling medium. The pocket 92″ is connected to the inside of the inner lining 50″ and surrounds the leg of the wearer.

I claim:

1. An athletic garment comprising:
(a) a single limb enclosing member;
(b) a neck band encircling the neck of the body; and
(c) yoke means supported by both shoulders of the body and interconnecting said band and said limb enclosing member for supporting said garment from the neck and both shoulders of the body of the user of said garment.

2. An athletic garment as claimed in claim 1 wherein said band has confronting free ends and said means is formed with separable sections detachably connected for the supporting of said garment from the user and for the removal of said garment from the user.

3. An athletic garment as claimed in claim 2 wherein said limb enclosing member includes at the free end thereof yieldable contraction means for encircling the limb of the user of said garment.

4. An athletic garment as claimed in claim 3 wherein said limb encircling member is in the form of a sleeve.

5. An athletic garment as claimed in claim 4 wherein said band is in the form of a collar.

6. An athletic garment as claimed in claim 1 wherein said band is an endless yieldable contraction band.

7. An athletic garment as claimed in claim 6 wherein said limb enclosing means includes at the free end thereof yieldable contraction means for encircling the limb of the user of said garment.

8. An athletic garment comprising:
(a) a limb enclosing member;
(b) a leak-proof pocket on said limb enclosing member arranged for holding a cooling medium for application to a limb of the user;
(c) a band encircling a portion of the body other than a limb; and
(d) means interconnecting said band and said limb enclosing member for supporting said garment from the user of said garment.

9. An athletic garment as claimed in claim 8 wherein said band has confronting free ends and means on said confronting free ends detachably connecting said free ends for the supporting of said garment from the user and for the removal of said garment from the user.

10. An athletic garment as claimed in claim 8 wherein said band is an endless yieldable contraction band.

11. An athletic garment as claimed in claim 8 wherein said limb enclosing member includes at the free ends thereof yieldable contraction means for encircling the limb of the user of said garment.

12. An athletic garment as claimed in claim 8 wherein said garment comprises a shell to which said means is attached.

13. An athletic garment as claimed in claim 8 wherein said limb enclosing member is in the form of a sleeve and said band is in the form of a collar.

14. An athletic garment as claimed in claim 8 wherein said limb enclosing member is in the form of a legging and said band encircles the waist of the body of the user.

15. An athletic garment as claimed in claim 14 wherein said band has confronting free ends and means on said confronting free ends detachably connecting said free ends for the supporting of said garment from the user and for the removal of said garment from the user.

16. An athletic garment as claimed in claim 8 wherein said pocket comprises a plurality of compartments in which said cooling medium is contained for application of the cooling medium to selected areas of a limb.

* * * * *